United States Patent [19]

Nishioka

[11] Patent Number: 5,598,205

[45] Date of Patent: Jan. 28, 1997

[54] IMAGING APPARATUS

[75] Inventor: Kimihiko Nishioka, Hachioji, Japan

[73] Assignee: Olympus Optical Co., Ltd., Tokyo, Japan

[21] Appl. No.: 231,176

[22] Filed: Apr. 22, 1994

[51] Int. Cl.$^6$ .............................. H04N 7/18; A61B 1/04; A61B 1/06

[52] U.S. Cl. ............... 348/65; 348/335; 359/720

[58] Field of Search .............. 348/65, 335, 294; 359/720; H04N 7/18

[56] References Cited

U.S. PATENT DOCUMENTS

| | | | |
|---|---|---|---|
| 4,467,361 | 8/1984 | Ohno | 348/65 |
| 4,916,534 | 4/1990 | Takahashi | 348/67 |
| 5,177,605 | 1/1993 | Takahashi | 348/65 |
| 5,184,223 | 2/1993 | Mihara | 348/207 |
| 5,329,310 | 7/1994 | Liljegren | 348/147 |

FOREIGN PATENT DOCUMENTS 5103271    4/1993    Japan .

*Primary Examiner*—Howard W. Britton
*Attorney, Agent, or Firm*—Cushman, Darby & Cushman, IP Group of Pillsbury Madison & Sutro LLP

[57] ABSTRACT

An imaging apparatus includes an objective lens system for forming an image of an object, a solid-state image pickup device, a signal processor and a display device. The objective lens system includes at least one revolutionally asymmetrical refractive surface for deforming the image formed by the objective lens system and is configured so as to deform further the image which is deformed by the signal processor.

8 Claims, 8 Drawing Sheets

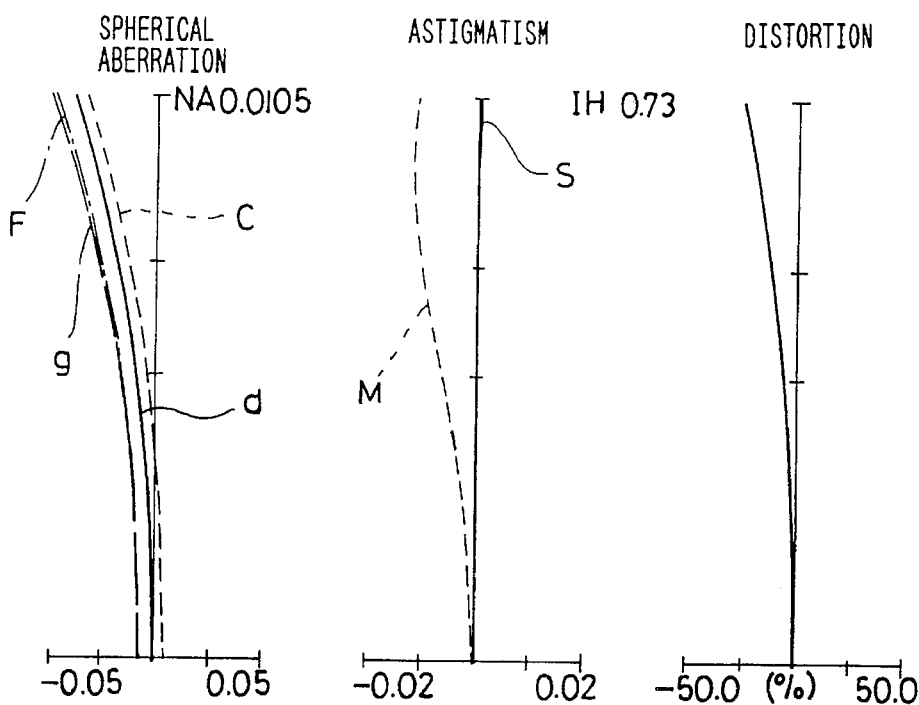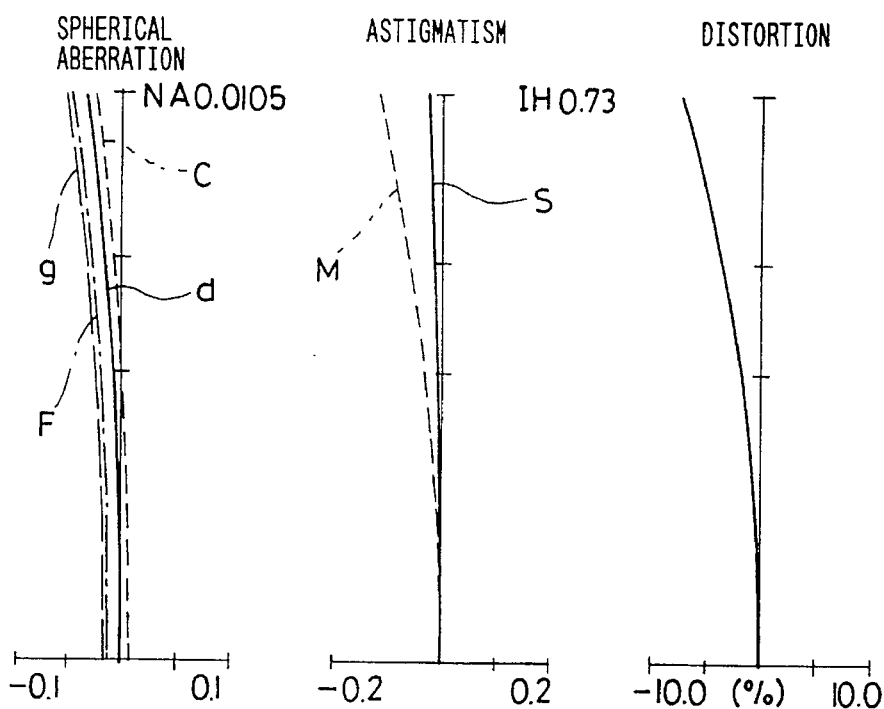

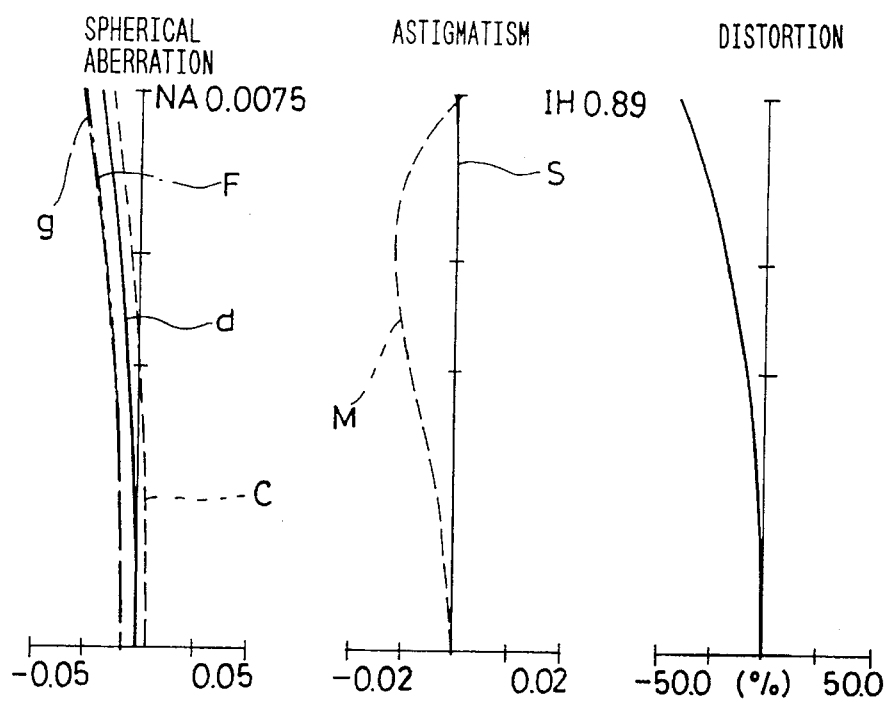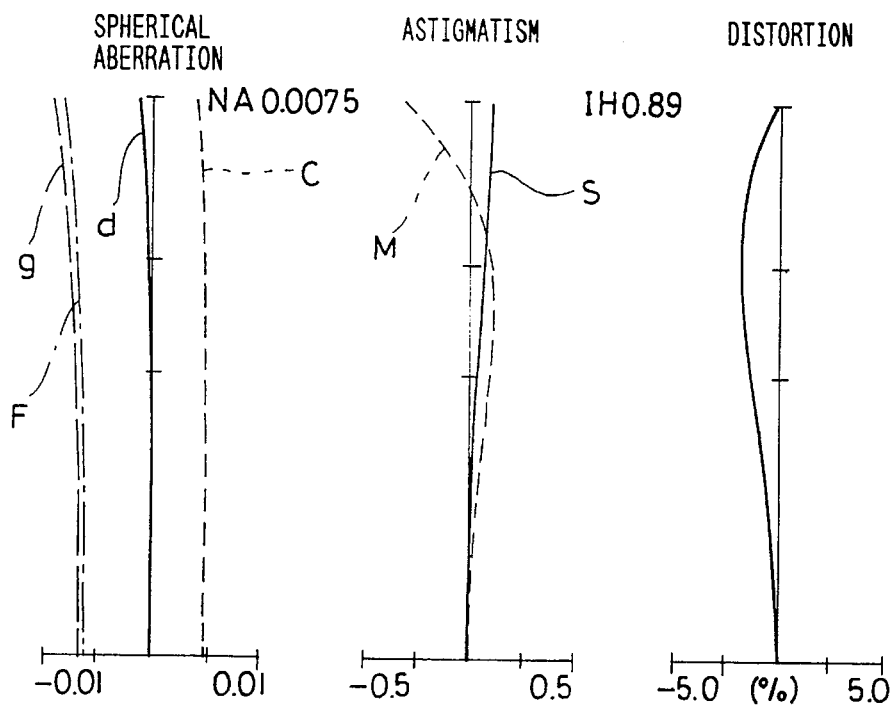

IMAGING APPARATUS

BACKGROUND OF THE INVENTION

1. Field of the Invention

The present invention relates to an imaging apparatus for electronic endoscopes.

2. Description of the Prior Art

The conventional electronic endoscope is mostly configured so as to form a image of an object by a circular lens system 32 on a nearly square image pickup device 31, process this image by an image processing circuit 33 and project a processed image 36 onto a display unit 35 of a TV monitor 34 as illustrated in FIG. 16.

The display unit 15 of the TV monitor 14 has a screen which is designed for an aspect ratio of H:V=4:3 in accordance with the current TV code (NTSC standard). Therefore, only a narrow screen area of the display unit 35 is used wastelessly when the image is projected to a partial area of the screen of the display unit 35 as shown in FIG. 16.

However, the high quality TV set adopts a display unit which has a screen designed for an aspect ratio of H:V=16:9, or is horizontally elongated. In case of an endoscope for the high quality TV set, a large screen area is utilized wastelessly when the square image formed by the electronic endoscope shown in FIG. 16 is projected onto the horizontally elongated screen of the display unit 15.

The problem of such wasteless use of the screen of the display unit can be solved by using a horizontally elongated solid-state image pickup device, but such a solid-state image pickup device will undesirably enlarge an outside diameter of an endoscope.

SUMMARY OF THE INVENTION

A primary object of the present invention is to provide an imaging apparatus configured so as to permit observing images which are made strongly appealing or highly impressive by effectively utilizing the horizontally elongated screen of the display unit of the high quality TV set.

The imaging apparatus according to the present invention comprises a nearly square solid-state image pick-up device, composed, for example, of CCD's, an objective lens system using at least one aspherical surface which is asymmetrical with regard to an optical axis and electrically elongating means.

A composition of the imaging apparatus according to the present invention is illustrated in FIG. 1, wherein the reference numeral 1 represents the solid-state image pickup device, the reference numeral 2 designates the objective lens system, the reference numeral 3 denotes a sampling circuit, the reference numeral 4 represents a hold circuit, the reference numeral 5 designates a video signal generating circuit, the reference numeral 6 denotes a TV monitor, the reference numeral 7 represents a display unit having a horizontally elongated screen, the reference numeral 8 designates a light source and the reference numeral 9 denotes a light guide fiber bundle.

In the imaging apparatus according to the present invention, the objective lens system having at least one aspherical surface which is revolutionally asymmetrical with regard to the optical axis functions to form an image of a rectangular range of an object on the solid-state image pickup device 1 which is nearly square.

Further, signals provided from the solid-state image pickup device 1 are read out by the sampling circuit 3 at a readout speed in the horizontal direction (a horizontal scanning direction) on the solid-state image pickup device 1 which is set at a level lower than the ordinary horizontal readout speed for elongating the image of the object in the horizontal direction.

Let us represent a vertical size and a horizontal size of the image of the object by $B_V$ and $B_H$ respectively, designate a vertical size and a horizontal size of the solid-state image pickup device 1 by $C_V$ and $C_H$ respectively, and denote numbers of picture elements of CCD's disposed in the horizontal direction and the vertical direction on the solid-state image pickup device 1 by $N_H$ and $N_V$ respectively. Then, the objective lens system 2 forms, on the solid-state image pickup device 1, an image which is contracted at a ratio multiplied by k expressed by the following formula (1):

$$(C_H/B_H)/(C_V/B_V) \equiv k \qquad (1)$$

$C_V/C_H$ is larger than V/H.

It is therefore possible to obtain a horizontally elongated image by selecting the readout speed 1/k times as high as the ordinary readout speed for reading out the signals provided from the solid-state image pickup device 1.

The image is not elongated in the horizontal direction when a number of the picture elements disposed in the vertical direction on the solid-state image pickup device 1 corresponds to a number $N_V$ of the scanning lines at a given average scanning times $T_H$ (≈33 microseconds) on the high quality TV set and a given aspect ratio A (≈16/9) of the display unit of the high quality TV set. That is to say, the picture elements disposed on the solid-state image pickup device 1 which is used in the ordinary manner are read out at a time interval $t_H$ expressed by the following formula (2):

$$t_H \approx N_V/N_{HD} \cdot C_H/C_V \cdot 1/A \cdot T_H/N_H \qquad (2)$$

This formula is obtained on an assumption that blanking periods are sufficiently short in both the horizontal direction and the vertical direction.

In the formula mentioned above, the reference symbol $N_{HD}$ represents a number of scanning lines in the vertical direction on the high quality TV set (1,125 in Japanese standard).

An image which is elongated k times as large in the horizontal direction can be obtained by reading out the signals provided from the solid-state image pickup device at intervals of $1/k \cdot t_H$ per picture element.

Signals which are sampled by the sampling circuit 3 are held by the hold circuit 4, then converted into luminance signals and color difference signals by the video signal generating circuit 5, and displayed on the display unit 7.

FIG. 2 shows another example of the imaging apparatus for magnifying, at a ratio 1/k times as high, an image which is contracted k times as large in one direction.

In this example, the video signals provided from the solid-state image pickup device 1 are stored once in a memory 10 and magnified 1/k times as large by a computerized image processing circuit 11.

This imaging apparatus can perform not only the magnification of an image 1/k times as large by the image processing circuit 11 but also correction of distortion produced by a lens system, thereby providing an image which is more correct than the image available with the imaging apparatus shown in FIG. 1. Further, the imaging apparatus shown in FIG. 2 can provide an image which is deformed as desired. In case of this imaging apparatus, signals of R.G.B.

code which are generated by a video signal generating circuit 12 are displayed on a TV monitor.

Now, description will be made of an objective lens system which is to be used in the imaging apparatus according to the present invention.

The objective lens system to be used in the imaging apparatus according to the present invention has magnifications which are different between the horizontal direction and the vertical direction, and satisfies the following condition (4):

$$\beta_z/\beta_y = k \qquad (4)$$

wherein the reference symbol $\beta_z$ represents the magnification in the horizontal direction and the reference symbol $\beta_y$ designates the magnification in the vertical direction.

The objective lens system is an anamorphic lens system which is shown in FIG. 3A and FIG. 3B, or a retrofocus type lens system having a composition in which at least one revolutionally asymmetrical aspherical surface ($A_S$) is disposed in each of sections located before and after an aperture stop. This aspherical surface ($A_S$) has a small radius of curvature in FIG. 3A which shows a sectional view taken in the horizontal direction (horizontal sectional view) but a large radius of curvature in FIG. 3B which shows a sectional view taken in the vertical direction (vertical sectional view) of the objective lens system.

The aspherical lens system having the aspherical surfaces $A_S$ described above has a form similar to that of a rugby ball as illustrated in FIG. 4 and is expressed by the following formula (5):

$$x = \frac{(1/R_i)(y^2 + z^2)}{1 + \sqrt{1 - (y^2 + z^2)/R_i^2}} + B_{yi}y^2 + B_{zi}z^2 + E_{1i}y^4 + \\ E_{2i}y^2z^2 + E_{3i}z^4 + F_{1i}y^6 + F_{2i}y^4z^2 + F_{3i}y^2z^4 + F_{4i}z^6 + G_{1i}y^8 + \\ G_{2i}y^6z^2 + G_{3i}y^4z^4 + G_{4i}y^2z^6 + G_{5i}z^8 + \ldots \qquad (5)$$

wherein the reference symbol i represents an ordinal number of a surface, the reference symbols x, y and z designate values on x, y and z axes respectively on an coordinates system on which the direction of the optical axis is taken as the x axis and a vertex of an aspherical surface is taken as an origin, the reference symbol $R_i$ denotes a radius of a reference sphere of the aspherical surface, the reference symbols $B_{yi}$, $B_{zi}$, . . . represent aspherical surface coefficients, and the reference symbols $E_{1i}$, $E_{2i}$, . . . designate aspherical surface coefficients.

This formula does not contain y and z of odd orders because the aspherical surface is symmetrical with regard to a horizontal section and a vertical section respectively. Further, the first term of the formula expresses a component of a centered spherical surface. The origin shown in FIG. 4 corresponds to the vertex of the aspherical surface. Further, radii of curvature $R_y$ and $R_z$ in the y and z directions on an elliptic paraboloid which is in contact with the vertex of the aspherical surface are given by the following formulae (6) and (7):

$$1/R_y = 2B_y \qquad (6)$$

$$1/R_z = 2B_z \qquad (7)$$

At least one aspherical surface expressed by the abovementioned formula (5) need be disposed in the objective lens system and it is advantageous to use two or more aspherical surfaces on both the sides of the stop as shown in FIG. 3 for correcting astigmatism, curvature of field and on-axis astigmatism Δ.

The on-axis astigmatism Δ means a distance as measured between a paraxial image point in the horizontal direction and another image point in the vertical direction, and an image will be blurred when the on-axis astigmatism Δ has a value which is not sufficiently small.

Conditions which are required for imparting a small value to the on-axis astigmatism Δ and enabling to contract an image in the horizontal direction will be described below:

Let us assume that anamorphic surfaces (toric surfaces) i and j, such as that shown in FIG. 4, are disposed before and after the stop respectively, represent refractive indices of media disposed before and after the surface i by $n_{i-1}$ and $n_i$ respectively, and designates refractive indices of media disposed before and after the surface k by $n_{j-1}$ and $n_j$ respectively. Then, the surfaces i and j have refractive powers in the horizontal direction (z direction) and vertical direction (v direction) which are defined as follows:

$$\phi_{yi} = 2(n_i - n_{i-1})B_{yi} \qquad (10)$$

$$\phi_{zi} = 2(n_i - n_{i-1})B_{zi} \qquad (11)$$

$$\phi_{yj} = 2(n_j - n_{j-1})B_{yj} \qquad (12)$$

$$\phi_{zj} = 2(n_j - n_{j-1})B_{zj} \qquad (13)$$

wherein the reference symbol $\phi_{yi}$ represents a refractive power of the surface i in the vertical direction, the reference symbol $\phi_{zi}$ designates a refractive power of the surface i in the horizontal direction, the reference symbol $\phi_{yj}$ denotes a refractive power of the surface j in the vertical direction and the reference symbol $\phi_{zj}$ represents a refractive power of the surface j in the horizontal direction.

For contracting an image in the horizontal direction, it is sufficient that the anamorphic surface disposed before the stop satisfies the condition (14) and that the anamorphic surface disposed after the stop satisfies the condition (15):

$$\phi_{yi} > \phi_{zi} \qquad (14)$$

$$\phi_{yj} < \phi_{zj} \qquad (15)$$

The anamorphic surfaces should be disposed in the vicinities of an object side lens component and an image side lens component respectively on which a principal ray is higher than a marginal ray.

For correcting the on-axis astigmatism Δ until it has a value of 0 in the objective lens system, on the other hand, it is necessary, from a viewpoint of its function to converge paraxial rays, to satisfy the following condition (16):

$$(\phi_{zi} - \phi_{yi})(\phi_{zj} - \phi_{yj}) < 0 \qquad (16)$$

The relationship expressed by the condition (16) establishes when the conditions (14) and (15) are satisfied.

By disposing the anamorphic surfaces satisfying the conditions (14) and (15) before and after the aperture stop respectively, it is therefore possible to obtain an objective lens system which forms an image contracted in the horizontal direction in which the on-axis astigmatism Δ has a small value.

When the objective lens system is to use three or more anamorphic surfaces including at least two which are to be disposed before and after the aperture stop respectively, it is necessary for contracting an iamge in the horizontal direction that any one of the anamorphic surfaces satisfies the condition (14) or (15).

For correcting the on-axis astigmatism Δ until it has a value of 0, at least a pair of surfaces m and n must satisfy the following condition (17):

$$(\phi_{zm}-\phi_{ym})(\phi_{zn}-\phi_{yn})<0 \tag{17}$$

wherein the reference symbol $\phi_{zm}$ represents a refractive power in the z direction of the surface m, the reference symbol $\phi_{ym}$ designate a refractive power in the y direction of the surface m, the reference symbol $\phi_{zn}$ denotes a refractive power in the z direction of the surface n and the reference symbol $\phi_{yn}$ represents a refractive power in the y direction of the surface n.

For correcting the on-axis astigmatism $\Delta$ until it has a value of 0 in a lens system comprising anamorphic surfaces, it is necessary to satisfy in place of the conditions (14) and (15), the following conditions (18) and (19):

$$\sum_{i=1}^{I} (\phi_{zi} - \phi_{yi}) < 0 \tag{18}$$

$$(i = 1, 2, \ldots, I)$$

$$\sum_{j=1}^{J} (\phi_{zj} - \phi_{yj}) > 0 \tag{19}$$

$$(j = 1, 2, \ldots, J)$$

Alternately, it is possible for reducing the on-axis astigmatism $\Delta$ to a value of 0 to replace the condition (17) with the following condition (20):

$$\sum_{n=1}^{N} (\phi_{zn}h_{zn} - \phi_{yn}h_{yn}) \approx 0 \tag{20}$$

wherein the reference symbols $h_{zn}$ and $h_{yn}$ represent the height of paraxial rays on the surface n in the z direction and the y direction respectively.

The condition (20) means that a total sum of angles of refraction for the paraxial rays in the z direction is equal to that in the y direction, and is required for reducing the on-axis astigmatism $\Delta$ until it has a value of 0. In practice, however, it is sufficient to satisfy the following condition (21) shown below in place of the condition (20):

$$\left| \sum_{n=1}^{N} (\phi_{zn}h_{zn} - \phi_{yn}h_{yn}) \right| < 1/3(\phi_{z}h_{z0} + \phi_{y}h_{y0}) \tag{21}$$

wherein the reference symbol $\phi_z$ represents a reverse number of $f_z$ which is a focal length in the z direction, the reference symbol $\phi_y$ designates an inverse number of $f_y$ which is a focal length in the y direction, and the reference symbols $h_{z0}$ and $h_{y0}$ denote heights of incidence of the paraxial rays on the first surface in the z direction and the y direction respectively.

A lens system which uses an anamorphic surface disposed only before or after the aperture stop cannot have both the functions to contract an image in the horizontal direction and reduce the on-axis astigmatism $\Delta$ to 0, but can exhibit an effect which is rather satisfactory since it can reduce the on-axis astigmatism $\Delta$ nearly to 0 when the marginal ray is lower than the principal ray on the anamorphic surface. For obtaining such an effect, the anamorphic surface should be disposed in the vicinity of a surface which is apart from the stop, i.e., an object side surface or an image side surface. The condition (14) should be satisfied when the anamorphic surface is disposed before the stop or the condition (15) should be satisfied when the anamorphic surface is disposed after the aperture stop.

When two or more anamorphic surfaces are to be disposed only before or after the aperture stop, it is possible to obtain the functions to contract an image in the horizontal direction and reduce the on-axis astigmatism $\Delta$ to 0 by configuring at least one of the anamorphic surfaces to be disposed before the aperture stop so that it satisfies the condition (14) or configuring at least one of the anamorphic surfaces to be disposed after the aperture stop so that it satisfies the condition (15).

For reducing the on-axis astigmatism $\Delta$ until it has a value of 0, it is necessary that at least a pair of surfaces k and l satisfy the following condition (22):

$$(\phi_{zk}-\phi_{yk})(\phi_{zl}-\phi_{zl})<0 \tag{22}$$

The anamorphic surfaces should desirably have shapes which are not circular at least in a horizontal section or a vertical section thereof so that optional shapes of aspherical surface can be selected for favorable correction of astigmatism.

A range allowable for the on-axis astigmatism selected for the examples described above is defined by the following formula (23):

$$\frac{1}{\sqrt{F_{Noy} F_{Noz}}} |\Delta| \leq 6 \sqrt{P_V \cdot P_H} \tag{23}$$

wherein the reference symbols $F_{Noy}$ and $F_{Noz}$ represent F numbers in the y direction and the z direction respectively, and the reference symbols $P_V$ and $P_H$ designate lengths in the horizontal direction and the vertical direction respectively of a single picture element of the CCD disposed on the solid-state image pickup device 1.

The solid-state image pickup device 1 should be disposed on the optical axis at a location in the middle of a paraxial image point in the horizontal direction and a paraxial image point in the vertical direction or a location slightly shifted from the middle location toward the lens system when curvature of field is taken into consideration.

BRIEF DESCRIPTION OF THE DRAWINGS

FIG. 9A, FIG. 9B and FIG. 9C show graphs illustrating aberration characteristics in the horizontal direction of the second embodiment of the lens system;

FIG. 10A, FIG. 10B and FIG. 10C show graphs visualizing aberration characteristics in the vertical direction of the first embodiment of the lens system;

FIG. 11A, FIG. 11B and FIG. 11C show curves illustrating aberration characteristics in the horizontal direction of the second embodiment of the lens system;

FIG. 12A, FIG. 12B and FIG. 12C show curves visualizing aberration characteristics in the vertical direction of the second embodiment of the lens system;

DETAILED DESCRIPTION OF THE PREFERRED EMBODIMENTS

Figure 1:
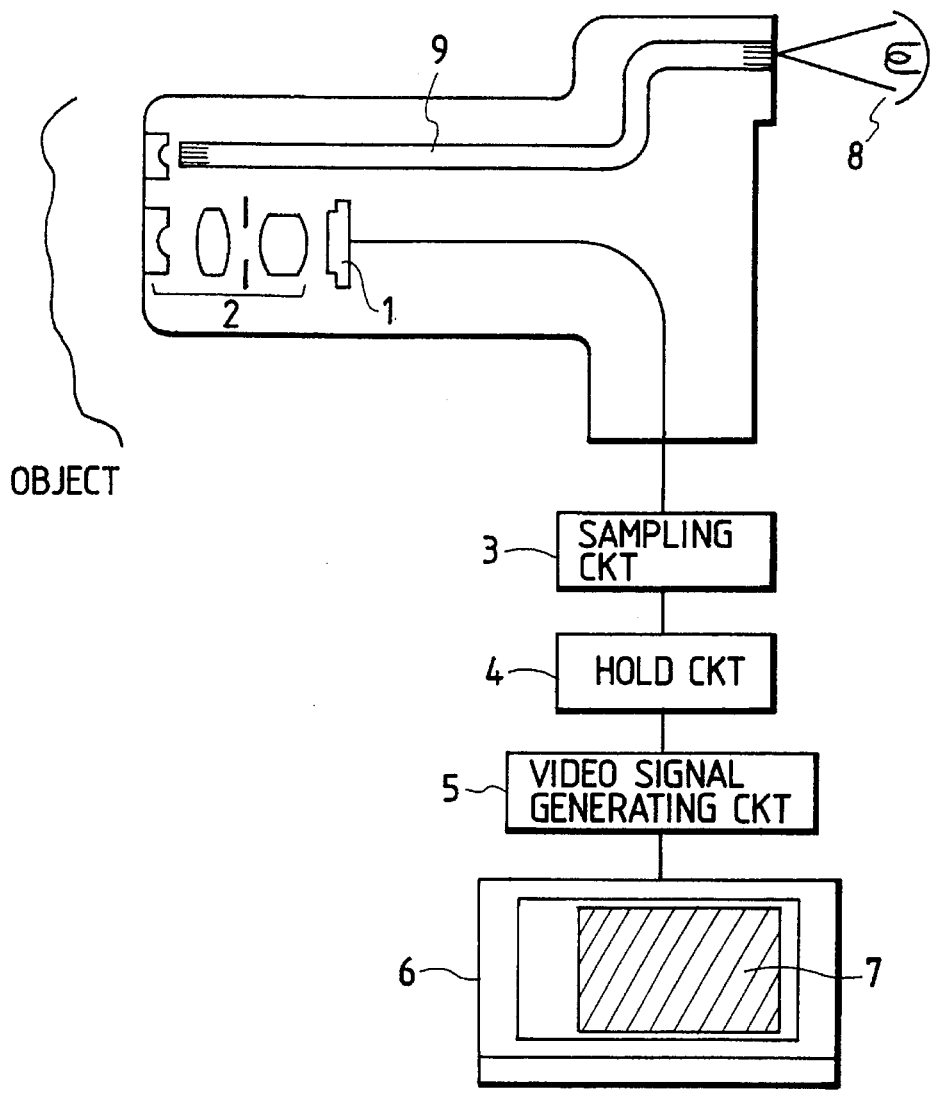
FIG. 1 shows a sectional view illustrating a composition of the imaging apparatus according to the present invention.
Figure 2:
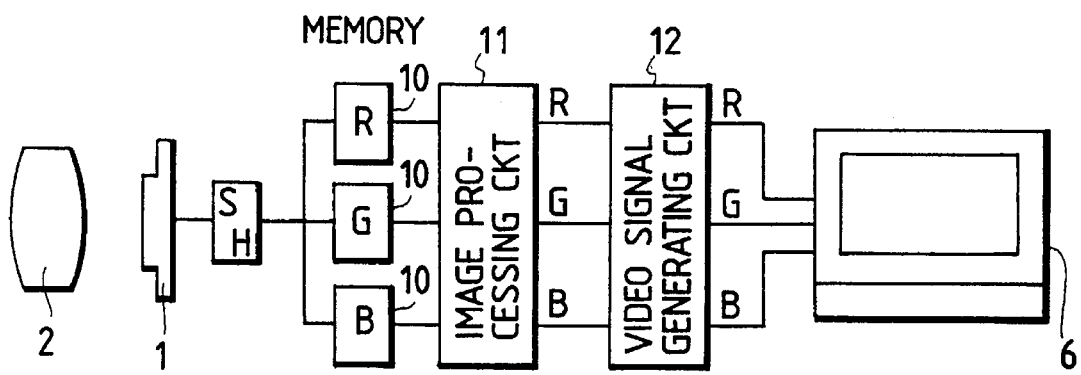
FIG. 2 shows a sectional view illustrating a composition of another example of the imaging apparatus according to the present invention.
Figure 3A:
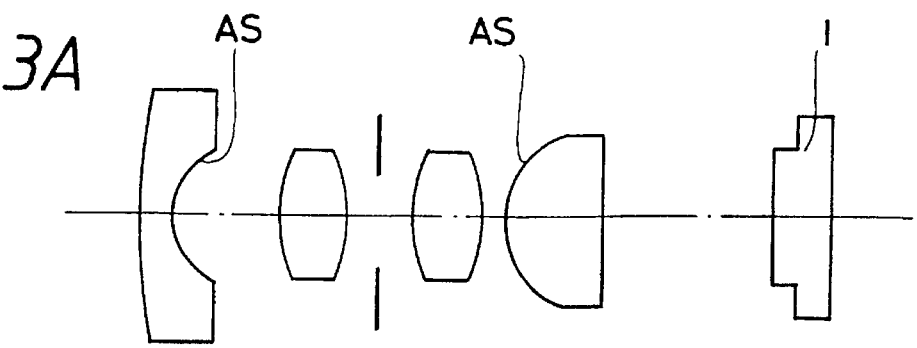
FIG. 3A and FIG. 3B show diagrams compositions of lens systems to be used in the imaging apparatus according to the present invention.
Figure 3B:
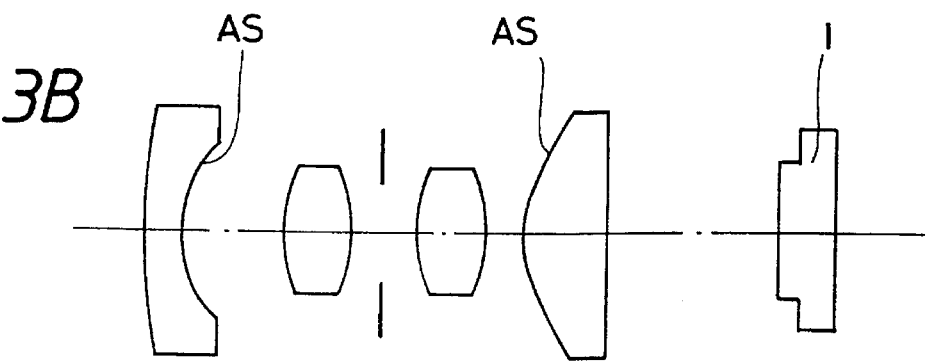
Figure 4:
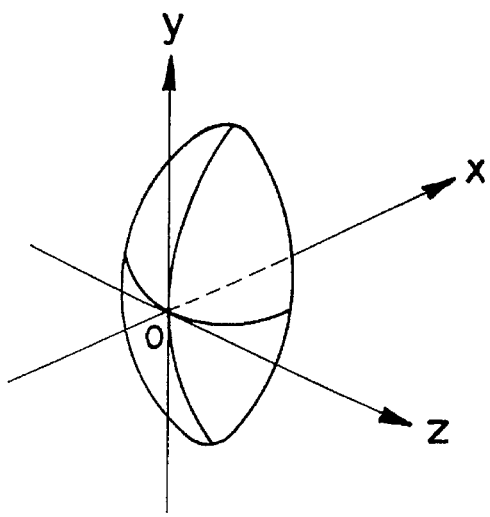
FIG. 4 shows a view illustrating a shape of an aspherical surface to be used in the lens systems shown in FIG. 3A and FIG. 3B.

Now, the imaging apparatus according to the present invention will be described in more detail below with reference to the preferred embodiments illustrated in the accompanying drawings and given in a form of the following numerical data:

Embodiment 1

(z direction)
$f_z=1.000$, $F_{Noz}=4.218$, $NA=-0.0105$, $\omega=43.874°$, $IH=0.7280$, $\beta_z=-0.08859$, $\phi_z=1.0$, object distance=$-10.8696$

| | | | |
|---|---|---|---|
| $r_1 = \infty$ | | | |
| | $d_1 = 0.3304$ | $n_1 = 1.88300$ | $v_1 = 40.78$ |
| $r_2 = 0.6783$ | | | |
| | $d_2 = 0.6000$ | | |
| $r_3 = 3.5348$ | | | |
| | $d_3 = 1.3652$ | $n_2 = 1.72916$ | $v_2 = 54.68$ |
| $r_4 = -1.3600$ | | | |
| | $d_4 = 0.0870$ | | |
| $r_5 = \infty$ (stop) | | | |
| | $d_5 = 0.3478$ | $n_3 = 1.52287$ | $v_3 = 59.89$ |
| $r_6 = \infty$ | | | |
| | $d_6 = 0.0261$ | | |
| $r_7 = \infty$ | | | |
| | $d_7 = 0.5391$ | $n_4 = 1.52000$ | $v_4 = 74.00$ |
| $r_8 = \infty$ | | | |
| | $d_8 = 0.1391$ | | |
| $r_9 = 2.9104$ | | | |
| | $d_9 = 1.2609$ | $n_5 = 1.69680$ | $v_5 = 55.52$ |
| $r_{10} = -0.9191$ | | | |
| | $d_{10} = 0.2609$ | $n_6 = 1.84666$ | $v_6 = 23.78$ |
| $r_{11} = -3.8252$ | | | |
| | $d_{11} = 0.0870$ | | |
| $r_{12} = \infty$ | | | |
| | $d_{12} = 0.3478$ | $n_7 = 1.52287$ | $v_7 = 59.89$ |
| $r_{13} = \infty$ | | | |
| | $d_{13} = 0.5739$ | | |
| $r_{14} = \infty$ | | | |
| | $d_{14} = 0.8696$ | $n_8 = 1.51633$ | $v_8 = 64.15$ |
| $r_{15} = \infty$ | | | | hight of paraxial ray
k   Y
1   0.114130

| | | | |
|---|---|---|---|
| | $d_4 = 0.0870$ | | |
| $r_5 = \infty$ (stop) | | | |
| | $d_5 = 0.3478$ | $n_3 = 1.52287$ | $v_3 = 59.89$ |
| $r_6 = \infty$ | | | |
| | $d_6 = 0.0261$ | | |
| $r_7 = \infty$ | | | |
| | $d_7 = 0.5391$ | $n_4 = 1.52000$ | $v_4 = 74.00$ |
| $r_8 = \infty$ | | | |
| | $d_8 = 0.1391$ | | |
| $r_9 = 2.9104$ | | | |
| | $d_9 = 1.2609$ | $n_5 = 1.69680$ | $v_5 = 55.52$ |

-continued

| | | | |
|---|---|---|---|
| $r_{10} = -0.9191$ | | | |
| | $d_{10} = 0.2609$ | $n_6 = 1.84666$ | $v_6 = 23.78$ |
| $r_{11} = -3.8252$ | | | |
| | $d_{11} = 0.0870$ | | |
| $r_{12} = \infty$ | | | |
| | $d_{12} = 0.3478$ | $n_7 = 1.52287$ | $v_7 = 59.89$ |
| $r_{13} = \infty$ | | | |
| (aspherical surface) | | | |
| | $d_{13} = 0.5739$ | | |
| $r_{14} = \infty$ | | | |
| | $d_{14} = 0.8696$ | $n_8 = 1.51633$ | $v_8 = 64.15$ |
| $r_{15} = \infty$ | | | |

(y direction)
$f_y=1.404$, $F_{Noy}=6.100$, $NA=-0.0105$, $\omega=27.596°$, $IH=0.7280$, $\beta_y=-0.12852$, $\phi_y=0.7122$, $\Delta=0.003$, object distance=$-10.8696$

| | | | |
|---|---|---|---|
| $r_1 = \infty$ | | | |
| (aspherical surface) | | | |
| | $d_1 = 0.3304$ | $n_1 = 1.88300$ | $v_1 = 40.78$ |
| $r_2 = 0.6783$ | | | |
| | $d_2 = 0.6000$ | | |
| $r_3 = 3.5348$ | | | |
| | $d_3 = 1.3652$ | $n_2 = 1.72916$ | $v_2 = 54.68$ |
| $r_4 = -1.3600$ | | | |
| | $d_4 = 0.0870$ | | |
| $r_5 = \infty$ (stop) | | | |
| | $d_5 = 0.3478$ | $n_3 = 1.52287$ | $v_3 = 59.89$ |
| $r_6 = \infty$ | | | |
| | $d_6 = 0.0261$ | | |
| $r_7 = \infty$ | | | |
| | $d_7 = 0.5391$ | $n_4 = 1.52000$ | $v_4 = 74.00$ |
| $r_8 = \infty$ | | | |
| | $d_8 = 0.1391$ | | |
| $r_9 = 2.9104$ | | | |
| | $d_9 = 1.2609$ | $n_5 = 1.69680$ | $v_5 = 55.52$ |
| $r_{10} = -0.9191$ | | | |
| | $d_{10} = 0.2609$ | $n_6 = 1.84666$ | $v_6 = 23.78$ |
| $r_{11} = -3.8252$ | | | |
| | $d_{11} = 0.0870$ | | |
| $r_{12} = \infty$ | | | |
| | $d_{12} = 0.3478$ | $n_7 = 1.52287$ | $v_7 = 59.89$ |
| $r_{13} = \infty$ | | | |
| (aspherical surface) | | | |
| | $d_{13} = 0.5739$ | | |
| $r_{14} = \infty$ | | | |
| | $d_{14} = 0.8696$ | $n_8 = 1.51633$ | $v_8 = 64.15$ |
| $r_{15} = \infty$ | | | | aspherical surface coefficients
(1st surface) B=0.14670, (13th surface) B=0.25000 hight of paraxial ray

| k | Y |
|---|---|
| 1 | 0.114503 |
| 2 | 0.111146 |
| 3 | 0.186486 |
| 4 | 0.255252 |
| 5 | 0.250925 |
| 6 | 0.239561 |
| 7 | 0.238263 |
| 8 | 0.220616 |
| 9 | 0.213693 |
| 10 | 0.138704 |
| 11 | 0.127643 |
| 12 | 0.118377 |
| 13 | 0.094040 |
| 14 | 0.046998 |
| 15 | −0.000008 |

$E_f=0$, $F_f=0$, $G_f=0$, $\phi_{y1}=0.25907$, $\phi_{y14}=-0.2614$, $\phi_{z1}=0$, $\phi_{z14}=0$  $(\phi_{zi}-\phi_{yi})\cdot(\phi_{zj}-\phi_{yj})=(-\phi_1)\cdot(-\phi_{14})=-0.06772<0$
$\Sigma(\phi_{zn}h_{zn}-\phi_{yn}h_{yn})=0.00508$,  $1/3(\phi_z h_{zo}+\phi_y h_{yo})=0.0653$, $\phi_{y1}h_{y1}=0.02966$, $\phi_{z1}h_{z1}=0$, $\phi_{y14}h_{y14}=-0.02458$, $\phi_{z14}h_{z14}=0$, $h_{yo}=h_{zo}=0.114503$, $\phi_{y}h_{yo}=0.08155$, $\phi_{z}h_{zo}=0.1145$

Embodiment 2

(z direction)
$f_z=1.000$, $F_{Noz}=5.906$, NA=−0.0075, $\omega=57.282°$, IH=0.8948, $\beta_z=-0.08859$, object distance=−10.8696

| | | | |
|---|---|---|---|
| $r_1 = \infty$ | | | |
| | $d_1 = 0.3304$ | $n_1 = 1.88300$ | $v_1 = 40.78$ |
| $r_2 = 0.6783$ | | | |
| | $d_2 = 0.6000$ | | |
| $r_3 = 3.5348$ | | | |
| | $d_3 = 1.3652$ | $n_2 = 1.72916$ | $v_2 = 54.68$ |
| $r_4 = -1.3600$ | | | |
| | $d_4 = 0.0870$ | | |
| $r_5 = \infty$ (stop) | | | |
| | $d_5 = 0.3478$ | $n_3 = 1.52287$ | $v_3 = 59.89$ |
| $r_6 = \infty$ | | | |
| | $d_6 = 0.0261$ | | |
| $r_7 = \infty$ | | | |
| | $d_7 = 0.5391$ | $n_4 = 1.52000$ | $v_4 = 74.00$ |
| $r_8 = \infty$ | | | |
| | $d_8 = 0.1391$ | | |
| $r_9 = 2.9104$ | | | |
| | $d_9 = 1.2609$ | $n_5 = 1.69680$ | $v_5 = 55.52$ |
| $r_{10} = -0.9191$ | | | |
| | $d_{10} = 0.2609$ | $n_6 = 1.84666$ | $v_6 = 23.78$ |
| $r_{11} = -3.8252$ | | | |
| | $d_{11} = 0.0870$ | | |
| $r_{12} = \infty$ | | | |
| | $d_{12} = 0.3478$ | $n_7 = 1.52287$ | $v_7 = 59.89$ |
| $r_{13} = \infty$ | | | |
| | $d_{13} = 0.5739$ | | |
| $r_{14} = \infty$ | | | |
| | $d_{14} = 0.8696$ | $n_8 = 1.51633$ | $v_8 = 64.15$ |
| $r_{15} = \infty$ | | | | hight of paraxial ray

| k | Y |
|---|---|
| 1 | 0.081522 |
| 2 | 0.082838 |
| 3 | 0.152044 |
| 4 | 0.218348 |
| 5 | 0.215471 |
| 6 | 0.207913 |
| 7 | 0.207050 |
| 8 | 0.195315 |
| 9 | 0.190711 |
| 10 | 0.132196 |
| 11 | 0.124117 |
| 12 | 0.116755 |
| 13 | 0.097417 |
| 14 | 0.048828 |
| 15 | 0.000276 |

(y direction)
$f_y=1.000$, $F_{Noy}=5.924$, NA=−0.0075, $\omega=41.248°$, IH=0.8948, $\beta_y=-0.08859$, $\Delta=0$, object distance=−10.8696

| | | | |
|---|---|---|---|
| $r_1 = \infty$ (aspherical surface) | | | |
| | $d_1 = 0.3304$ | $n_1 = 1.88300$ | $v_1 = 40.78$ |
| $r_2 = 0.6783$ | | | |
| | $d_2 = 0.6000$ | | |
| $r_3 = 3.5348$ | | | |
| | $d_3 = 1.3652$ | $n_2 = 1.72916$ | $v_2 = 54.68$ |
| $r_4 = -1.3600$ | | | |
| | $d_4 = 0.0870$ | | |
| $r_5 = \infty$ (stop) | | | |
| | $d_5 = 0.3478$ | $n_3 = 1.52287$ | $v_3 = 59.89$ |
| $r_6 = \infty$ | | | |
| | $d_6 = 0.0261$ | | |
| $r_7 = \infty$ | | | |
| | $d_7 = 0.5391$ | $n_4 = 1.52000$ | $v_4 = 74.00$ |
| $r_8 = \infty$ | | | |
| | $d_8 = 0.1391$ | | |
| $r_9 = 2.9104$ | | | |
| | $d_9 = 1.2609$ | $n_5 = 1.69680$ | $v_5 = 55.52$ |
| $r_{10} = -0.9191$ | | | |
| | $d_{10} = 0.2609$ | $n_6 = 1.84666$ | $v_6 = 23.78$ |
| $r_{11} = -3.8252$ (aspherical surface) | | | |
| | $d_{11} = 0.0870$ | | |
| $r_{12} = \infty$ | | | |
| | $d_{12} = 0.3478$ | $n_7 = 1.52287$ | $v_7 = 59.89$ |
| $r_{13} = \infty$ | | | |
| | $d_{13} = 0.5739$ | | |
| $r_{14} = \infty$ | | | |
| | $d_{14} = 0.8696$ | $n_8 = 1.51633$ | $v_8 = 64.15$ |
| $r_{15} = \infty$ | | | | aspherical surface coefficients
(1st surface) E=0.13000, (11th surface) E=0.18000 hight of paraxial ray

| k | Y |
|---|---|
| 1 | 0.081275 |
| 2 | 0.082587 |
| 3 | 0.151583 |
| 4 | 0.217686 |
| 5 | 0.214818 |
| 6 | 0.207284 |
| 7 | 0.206423 |
| 8 | 0.194723 |
| 9 | 0.190134 |
| 10 | 0.131796 |
| 11 | 0.123741 |
| 12 | 0.116401 |
| 13 | 0.097122 |
| 14 | 0.048680 |
| 15 | 0.000275 |

$B_{y1}=B_{z1}=F_{j1}=G_{j1} \ldots =0$, $E_{11}=0.13$, $E_{21}=0.065$, $E_{31}=0$, $E_{114}=0.18$, $E_{214}=0.09$, $E_{314}=0$, $B_{y14}=B_{z14}=F_{j14}=G_{j14} \ldots =0$ (j=1,2,3, ...)

wherein the reference symbols $r_1$, $r_2$, ... represent radii of curvature on surfaces of respective lens elements, the reference symbols $d_1$, $d_2$, ... designate thicknesses of the respective lens elements and airspaces reserved therebetween, the reference symbols $n_1$, $n_2$, ... denote refractive indices of the respective lens element, and the reference symbols $v_1$, $v_2$, ... represent Abbe's numbers of the respective lens elements.

Figure 5:
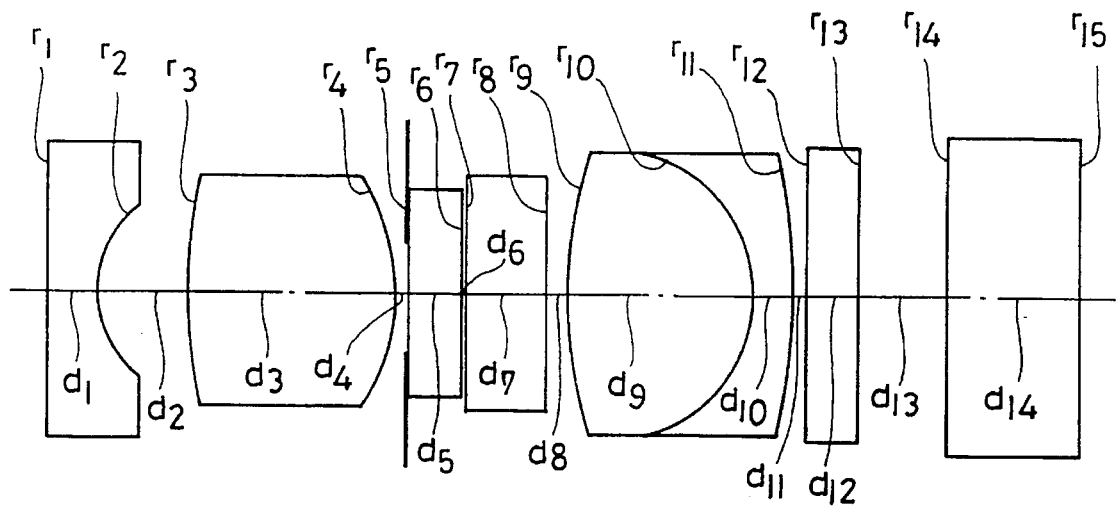
FIG. 5 shows a horizontal sectional view illustrating a composition of a first embodiment of the lens system to be used in the imaging apparatus according to the present invention.
Figure 6:
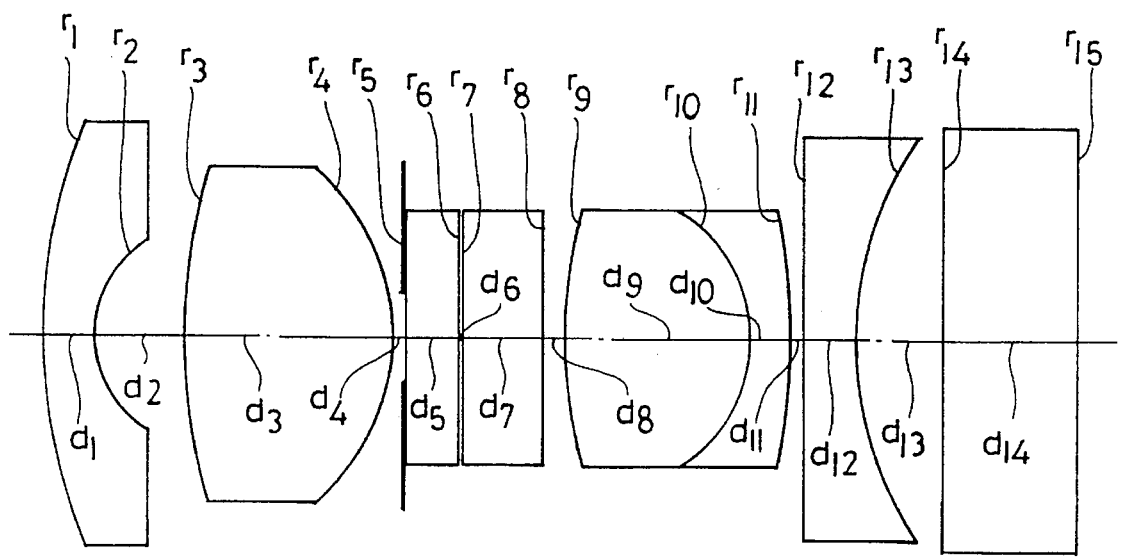
FIG. 6 shows a vertical sectional view illustrating the first embodiment of the lens system.

The first embodiment of the present invention has the composition which is illustrated in the sectional view in the z direction shown in FIG. 5 and the sectional view in the y direction shown in FIG. 6. The first embodiment uses two cylindrical lens components which are disposed before and after an aperture stop respectively so that it can form an image of a rectangular range of an object on a square solid-state image pickup device.

$\beta_H$ has a value which is the same as that of $\beta_z$ and $\beta_V$ has a value which is the same as that of $\beta_y$.

The lens system used in the first embodiment is specified for $\beta_z=-0.08859$, $\beta_y=-0.12852$ or $\beta_z/\beta_y=0.6893\approx9/16\approx0.5625$.

Though the value of $\beta_z/\beta_y$ seems to be different from 9/19, the half field angle $\omega_H$ in the horizontal direction is −43°87 and the half field angle $\omega_V$ in the vertical direction is −27°596, whereby an image of a rectangular range of an object has an aspect ratio defined below:

$$\tan 27°596/\tan 43°87=0.5437\approx9/16$$

Therefore, the aspect ratio of the image obtained is matched with the aspect ratio of the display unit screen of the high quality TV set.

The difference between the value of $\beta_z/\beta_y$ and 9/16 is produced due to distortion.

Therefore, $\beta_z/\beta_y$ may practically have a value which is rather different from 9/16. Even when possibility to use the display unit for displaying data such as characters together with an image, it is sufficient that $\beta_z/\beta_y$ has a value within a range defined by the following condition (24):

$$0.25 < \beta_z/\beta_y < 0.97 \tag{24}$$

Figure 7:
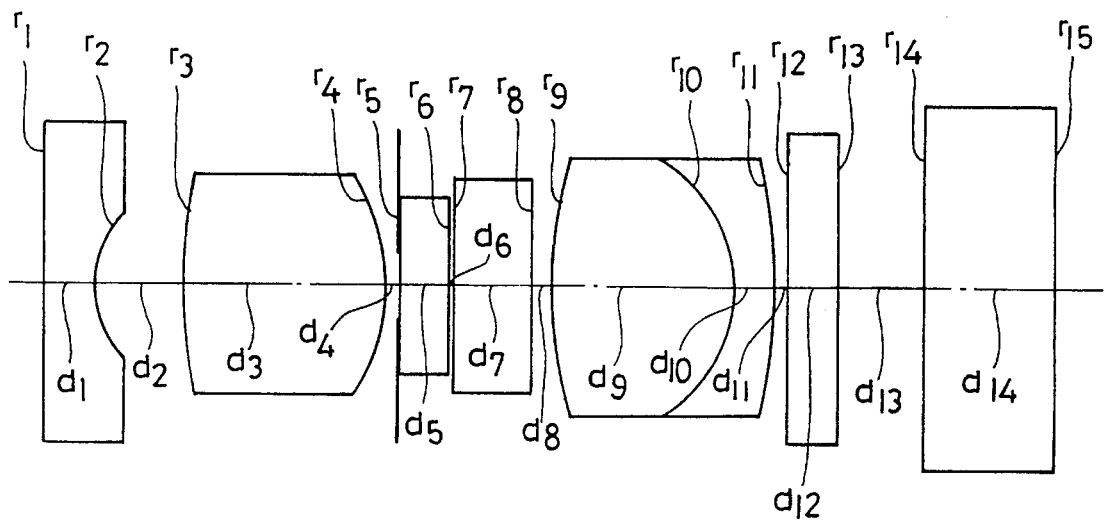
FIG. 7 shows a horizontal sectional view illustrating a second embodiment of the lens system to be used in the iamging apparatus according to the present invention.
Figure 8:
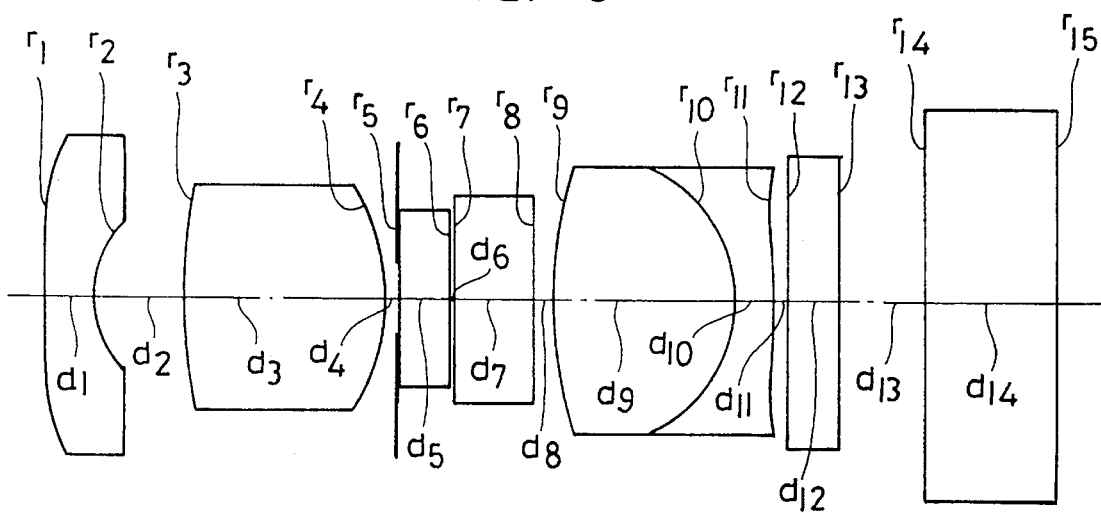
FIG. 8 shows a vertical sectional view illustrating the second embodiment of the lens system.

FIG. 7 and FIG. 8 show sectional views in the y direction and the z direction respectively illustrating the composition of the second embodiment of the lens system which is to be used in the imaging apparatus according to the present invention.

The second embodiment has a vertical paraxial magnification which is equal to a horizontal paraxial magnification thereof and produces distortion in the z direction in an amount modified so as to form an image of a rectangular range of an object which is contracted in the horizontal direction.

In the second embodiment, an aspherical surface which has a revolutionally asymmetrical component in the term of the fourth order is disposed in each of the sections before and after the stop.

When the aspherical surface disposed before the aperture stop is represented by an ordinal number p and the aspherical surface disposed after the aperture stop is designated by an ordinal number q, we obtain:

$$E_{1p}(n_p - n_{p-1}) = \phi_{yp} \tag{25}$$

$$E_{3p}(n_p - n_{p-1}) = \phi_{zp} \tag{26}$$

(For formula (25) and (26) can be defined similarly for the surface q by replacing p with q.) It is desirable for reducing curvature of field in each of the y and z directions to satisfy the conditions (27) and (28):

$$\phi_{yp} \cdot \phi_{yq} < 0 \tag{27}$$

$$\phi_{zp} \cdot \phi_{zq} < 0 \tag{28}$$

This is because the fourth order term $E_{ap}$ (a=1 or 3) of the formula expressing aspherical surfaces influences on the third order astigmatism $A_p$ to be produced by the surface p as expressed below:

$$A_p = 8 h_{ap}^2 \cdot h_{bp}^2 \cdot \phi_{yp} \tag{29}$$

Similarly, the surface q produces third order astigmatism $A_q$ as expressed below:

$$A_q = 8 h_{aq}^2 \cdot h_{bq} \cdot \phi_{yp} \tag{30}$$

The reference symbols $h_{ap}$ and $h_{bp}$ used in the above-mentioned formula (29) represent heights of the paraxial marginal ray and paraxial principal ray respectively on the surface p. Similarly, the reference symbols $h_{aq}$ and $h_{bq}$ used in the formula (30) represent heights of the paraxial marginal ray and the paraxial principal ray on the surface q.

Form the formulae (29) and (30), $\phi_{yp}$ and $\phi_{yq}$ must have signs different from each other for obtaining $A_p + A_q \approx 0$.

Similarly, $\phi_{zp}$ and $\phi_{zq}$ in the z direction must have signs which are also different from each other.

The second embodiment is specified for $\beta_y = \beta_z$ and $f_y = f_z$ so as to reduce the on-axis astigmatism $\Delta$ to 0, and has a half field angle $\omega_H$ in the horizontal direction = 57°282 and a field angle $\omega_V$ in the vertical direction = 41°248.

As a result, the second embodiment provides an aspect ratio defined below:

$$(\tan \omega_H / \tan \omega_V)^{-1} = 0.5634 \approx 9/16$$

That is to say, the second embodiment is an example for controlling field angles in the horizontal direction and the vertical direction by controlling distortion.

The second embodiment reduces the on-axis astigmatism $\Delta$ to 0 and features high resolution at a center of a visual field which is important for observation.

Though the foregoing description has been made of the present invention for its applicability to the imaging apparatus which is used for observing images on TV monitors using solid-state image pickup device, the present invention is also applicable to electronic endoscopes or similar instruments which are to be used for observing images on TV monitors by utilizing solid-state image pickup devices.

Figure 13:
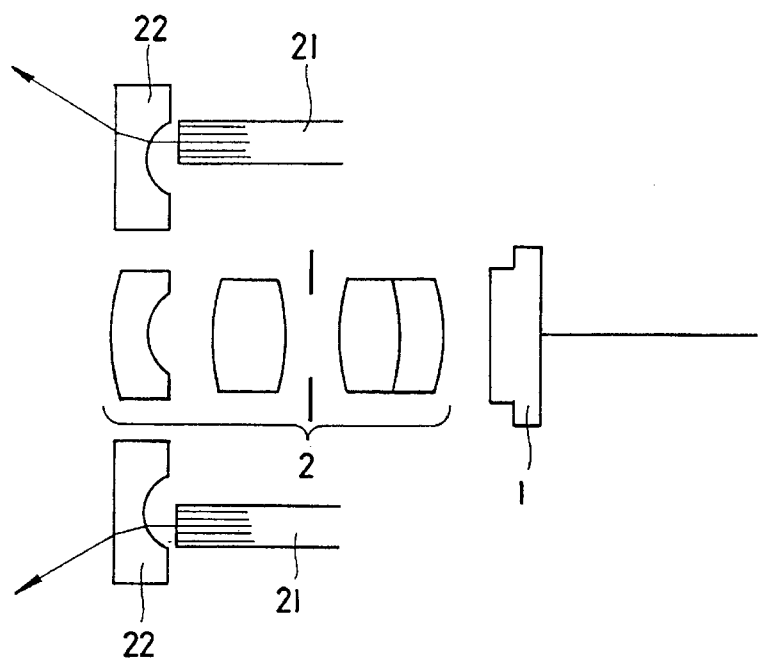
FIG. 13 shows a sectional view illustrating a composition of an illumination optical system to be used for an electronic endoscope which comprises the imaging apparatus according to the present invention.

FIG. 13 shows a sectional view illustrating an illumination optical system to be used with the imaging apparatus according to the present invention when it is combined with an electronic endoscope. Since the imaging apparatus according to the present invention forms a horizontally elongated image, the illumination optical system must illuminate a rectangular range of an object. FIG. 13 exemplifies such an illumination system wherein a concave lens component 22 disposed before a light guide fiber bundle 21 is eccentric in the z direction with regard to the light guide fiber bundle for broadening an illumination light bundle in the z direction. For obtaining such a function, it is desirable to shift the concave lens component 22 inward with regard to the light guide fiber bundle, or in the z direction as shown in FIG. 13.

Figure 14:
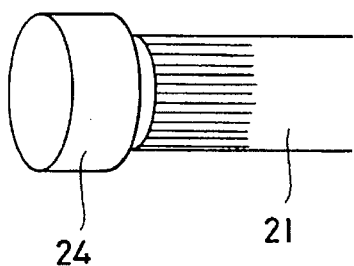
FIG. 14 shows a perspective view of another example of the illumination optical system to be used in the electronic endoscope.
Figure 15A:
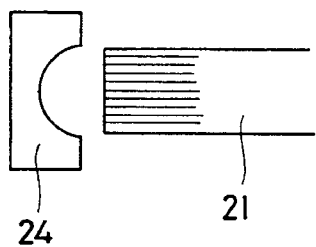
FIG. 15A and FIG. 15B show a horizontal sectional view and a vertical sectional view respectively of the illumination optical system shown in FIG. 14.
Figure 15B:
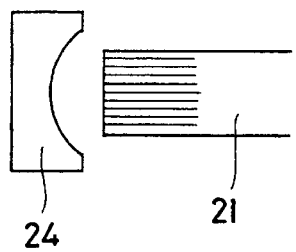
Figure 16:
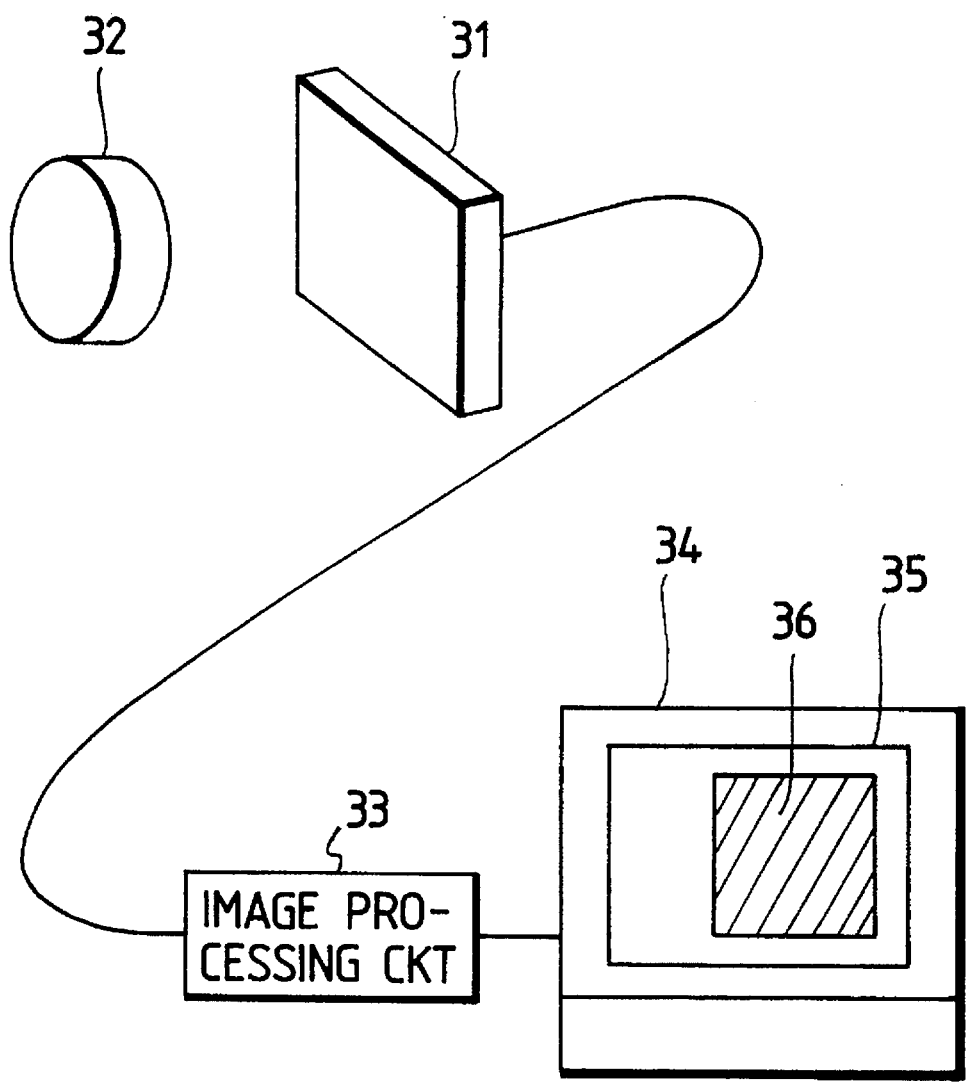
FIG. 16 shows a view schematically illustrating a configuration of the conventional imaging apparatus.

FIG. 14 shows another example of an illumination optical system which is to be used with the imaging apparatus according to the present invention and comprises an anamorphic concave lens component disposed before a light guide fiber buundle having a circular end surface. FIG. 15A and FIG. 15B show a horizontal sectional view and a vertical sectional view respectively of the illumination optical system shown in FIG. 14. As is seen from FIG. 15A and FIG. 15B, the anamorphic concave lens component has a refractive power in the vertical direction which is weaker than that in the horizontal direction. A shape of this lens component is also expressed by the formula (5). An illumination light bundle which is broadened in the horizontal direction can be obtained also by using a light guide fiber bundle which has a circular sectional shape as shown in these drawings.

When a vertical focal length of an illumination lens is represented by $f_{VL}$ and a horizontal focal length of the illumination lens is designated by $f_{HL}$, it is desirable to satisfy the relationship expressed by the following formula (36):

$$H : V \approx f_{HL} : f_{VL} \tag{36}$$

The relationship expressed by the formula (36) is satisfied even when the illumination lens is anamorphic.

The imaging apparatus according to the present invention can be combined not only with electronic endoscopes but also TV cameras and electronic cameras. Further, the imaging apparatus according to the present invention does not always require correction of image shapes or permits modifying image shapes as occasion demands. Furthermore, the imaging apparatus according to the present invention is applicable not only to the high quality TV sets but also to TV sets which are designed in accordance with the NTSC standard and the PAL standard, and compatible with display screens which are not square.

The imaging apparatus according to the present invention is applicable even when solid-state image pickup devices have shapes similar to those of display units of TV monitors or when images to be displayed are modified for displaying data such as characters additionally.

In addition, the imaging apparatus according to the present invention can be configured so as to form an image, at a ratio modified between two obliquely intersecting directions instead of the aspect ratio, which is to be deformed by an electronic circuit and then displayed on a TV monitor. In such a case, magnifications in the two obliquely intersecting directions correspond to $\beta_H$ and $\beta_V$ used in the foregoing description, and these two directions correspond to the y and z directions.

It is desirable for the imaging apparatus according to the present invention to use a solid-state image pickup device having picture elements each of which has a horizontal size longer than a vertical size thereof since picture elements disposed at a high density in the horizontal direction are preferable for the imaging apparatus which forms a horizontally elongated image. A solid-state image pickup device using such picture elements will find a hopeful future since the NTSC standard is to be modified for adopting such a solid-state image pickup device. Since such a solid-state image pickup device has an aspect ratio of 4/3, the formulae adopted by the present invention are applicable with a simple modification to A=4/3 as well as modifications of the formulae (29) and (30) into (31) and (32) respectively:

$$\beta_z/\beta_y \approx 1/A = 0.75 \tag{31}$$

$$(\tan \omega_H/\tan \omega_V)^{-1} \approx 1/A = 0.75 \tag{32}$$

The present invention provides a compact imaging apparatus which permits displaying strongly appealing or highly impressive image on a TV monitor.

Further, anamorphic lens components may be used to form images having different ratios between vertical sizes and horizontal sizes on rectangular solid-state image pickup devices. Anamorphic lens components may be used, for example, to form images of objects at a ratio of approximately 9:16 between vertical sizes and horizontal sizes on solid-state image pickup devices in accordance with the NTSC standard which generally have rectangular shapes having a ratio of 3:4 between vertical sizes and horizontal sizes and are available rather easily. In this case, a ratio between a magnification in the z direction and a magnification in the y direction will be as calculated by the following equation (33):

$$\frac{\beta_z}{\beta_y} \approx \frac{9/16}{3/4} = \frac{3}{4} \tag{33}$$

Considering possibilities that images are not displayed over entire ranges of screens of display units to reserve some areas for displaying characters and other data, that images are influenced due to distortion, and that allowances of actual magnification errors are rather large for images of objects of certain kinds, the ranges defined by the formulae (31) and (32) may be replaced with that specified by the formula (34) shown below, and the range defined by the formula (32) may be replaced with that defined by the following formula (35):

$$0.35 < \frac{\beta_z}{\beta_y} < 1.0 \tag{34}$$

$$0.35 \left( \frac{\tan \omega H}{\tan \omega V} \right)^{-1} < 1.0 \tag{35}$$

I claim:

1. An imaging apparatus comprising: an objective lens system for forming an image of an object, a solid-state image pickup device for receiving the image formed by said objective lens system, a signal processing means for generating video signals from signals output from said solid-state image pickup device and a display means for displaying an image of the object by using said video signals; wherein said objective lens system comprises at least one revolutionally asymmetrical refracting surface expressed by the formula (5) shown below for projecting a deformed image of said object onto said solid-state image pickup device and wherein said signal processing means further deforms signals of the deformed image provided from said solid-state image pickup device for displaying an image of the object on said display means, $$x = \frac{(1/R_i)(y^2 + z^2)}{1 + \sqrt{1 - (y^2 + z^2)/R_i^2}} + B_{yi}y^2 + B_{zi}z^2 + E_{1i}y^4 + \\ E_{2i}y^2z^2 + E_{3i}z^4 + F_{1i}y^6 + F_{2i}y^4z^2 + F_{3i}y^2z^4 + F_{4i}z^6 + G_{1i}y^8 + \\ G_{2i}y^6z^2 + G_{3i}y^4z^4 + G_{4i}y^2z^6 + G_{5i}z^8 + \ldots \tag{5}$$

wherein the reference symbol i represents an ordinal number of a surface, the reference symbol x, y and z designate values on x, y and z axes respectively on an coordinates system on which a direction of an optical axis is taken as the x axis and a vertex of the refractive surface is taken as an origin, the reference symbol $R_i$ denotes a radius of curvature of a reference sphere of the refractive surface, the reference symbols $B_{yi}$, $B_{zi}$, ... represent aspherical surface coefficients, and the reference symbols $E_{1i}$, $E_{2i}$, ... designate aspherical surface coefficients.

2. An electronic endoscope comprising:

an illuminating means for illuminating an object, an objective lens system for forming an image of the object, a solid-state image pickup device for receiving the image formed by said objective lens system, signal processing means for generating video signals from signals output from said solid-state image pickup device, and display means for displaying an image of the object by using said video signals;

wherein said objective lens system has at least one revolutionally asymmetrical refractive surface for projecting a deformed image of the object onto said solid-state image pickup device, wherein said signal processing means further deforms signals of the deformed image provided from said solid-state image pickup device for displaying an image of the object on said display means, and wherein the revolutionally asymmetrical refractive surface disposed in said objective lens system is expressed by the following formula:

$$x = \frac{(1/R_i)(y^2 + z^2)}{1 + \sqrt{1 - (y^2 + z^2)/R_i^2}} + B_{yi}y^2 + B_{zi}z^2 + E_{1i}y^4 + \tag{5}$$

-continued
$$E_{2i}y^2z^2 + E_{3i}z^4 + F_{1i}y^6 + F_{2i}y^4z^2 + F_{3i}y^2z^4 + F_{4i}z^6 + G_{1i}y^8 +$$
$$G_{2i}y^6z^2 + G_{3i}y^4z^4 + G_{4i}y^2z^6 + G_{5i}z^8 + \ldots$$

wherein the reference symbol i represents an ordinal number of a surface, the reference symbol x, y and z designate values on x, y and z axes respectively on a coordinates system on which a direction of an optical axis is taken as the x axis and a vertex of the refractive surface is taken as an origin, the reference symbol $R_i$ denotes a radius of curvature of a reference sphere of the refractive surface, the reference symbols $B_{yi}$, $B_{zi}$, . . . represent aspherical surface coefficients, and the reference symbols $E_{1i}$, $E_{2i}$, . . . designate aspherical surface coefficients.

3. An imaging apparatus according to claim 1 or 2 wherein said objective lens system comprises an aperture stop, said revolutionally asymmetrical refractive surface is disposed on the object side of said aperture stop and said imaging apparatus satisfies the following condition:

$$\phi_{yi} > \phi_{zi} \tag{14}$$

wherein $\phi_{yi} = 2(n_i - n_{i-1}) B_{yi}$ (10), $\phi_{zi} = 2(n_i - n_{i-1}) B_{zi}$ (11) and the reference symbols $n_{i-1}$ and $n_i$ represent refractive indices of media located on the object side and the image side respectively of said revolutionally asymmetrical refractive surface.

4. An imaging apparatus according to claim 1 or 2 wherein said objective lens system comprises an aperture stop, said revolutionally asymmetrical refractive surface is disposed on the image side of said aperture stop and said imaging apparatus satisfies the following condition:

$$\phi_{yi} < \phi_{zi} \tag{15}$$

wherein $\phi_{yi} = 2(n_i - n_{i-1}) B_{yi}$ (10), $\phi_{zi} = 2(n_i - n_{i-1}) B_{zi}$ (11), the reference symbols $n_{i-1}$ and $n_i$ represent refractive indices of media located on the object side and the image side respectively of said revolutionally asymmetrical surface.

5. An imaging apparatus according to claim 1 or 2 wherein said objective lens system comprises a plurality of revolutionally asymmetrical refracting surfaces and said imaging apparatus satisfies the following condition:

$$(\phi_{zi} - \phi_{yi})(\phi_{zj} - \phi_{yj}) < 0$$

wherein $\phi_{yi} = 2(n_i - n_{i-1}) B_{yi}$, $\phi_{zi} = 2(n_i - n_{i-1}) B_{zi}$, and the reference symbols $n_{i-1}$ and $n_i$ represent refractive indices of media located on the object side and the image side respectively of a revolutionally asymmetrical surface i, and the reference symbols $n_{j-1}$ and $n_j$ designate refractive indices of media located on the object side and the image side respectively of another revolutionally asymmetrical refractive surface j.

6. An imaging apparatus according to claim 1 or 2 wherein said objective lens system comprises an aperture stop, a plurality of revolutionally asymmetrical refractive surfaces are disposed on the object side of said aperture stop, and said imaging apparatus satisfies the following condition:

$$\Sigma(\phi_{zi} - \phi_{yi}) < 0 \tag{18}$$

wherein $\phi_{yi} = 2(n_i - n_{i-1}) B_{yi}$, $\phi_{zi} = 2(n_i - n_{i-1}) B_{zi}$ and the reference symbols $n_{i-1}$ and $n_i$ represent refractive indices of media located on the object side and the image side respectively of each of said revolutionally asymmetrical refractive surfaces.

7. An imaging apparatus according to claim 1 or 2 wherein said objective lens system comprises an aperture stop, a plurality of revolutional asymmetrical surfaces are disposed on the image side of said aperture stop and said imaging apparatus satisfies the following condition:

$$\Sigma(\phi_{zi} - \phi_{yi}) > 0 \tag{15}$$

wherein $\phi_{yi} = 2(n_i - n_{i-1}) B_{yi}$, $\phi_{zi} = 2(n_i - n_{i-1}) B_{zi}$ and the reference symbols $n_{i-1}$ and $n_i$ represent refractive indices of media located on the object side and the image side respectively of each of said revolutionally asymmetrical surfaces.

8. An imaging apparatus according to claim 1 or 2 wherein said objective lens system comprises a plurality of revolutionally asymmetrical refractive surfaces and said imaging apparatus satisfies the following condition:

$$|\Sigma(\phi_{zn}h_{zn} - \phi_{yn}h_{yn})| < 1/3(\phi_z h_{z0} + \phi_y h_{y0})$$

wherein $\phi_{yn} = 2(n_n - n_{n-1}) B_{yn}$, $\phi_{zn} = 2(n_n - n_{n-1}) B_{zn}$, the reference symbols $n_{n-1}$ and $n_n$ represent refractive indices of media located on the object side and image side respectively of a revolutionally asymmetrical refractive surface n, the reference symbols $n_{m-1}$ and $n_m$ designate refractive indices of media located on the object side and the image side respectively of another revolutionally asymmetrical surface m, the reference symbols $h_{zn}$ and $h_{yn}$ denotes heights of a paraxial ray in the z and y directions respectively on the refractive surface n, the reference symbols $h_{zm}$ and $h_{ym}$ represent heights of the paraxial ray in the z and y directions respectively on the refractive surface m, and the reference symbols $h_{z0}$ and $h_{y0}$ designate heights of the paraxial ray in the z and y directions respectively on a first surface of said objective lens system.

\* \* \* \* \*